(12) United States Patent  (10) Patent No.: US 8,010,195 B2
Sunagawa et al.  (45) Date of Patent: Aug. 30, 2011

(54) CARDIAC PACING SYSTEM BY SUBSTITUTING NATIVE BIOLOGICAL REGULATORY FUNCTION

(75) Inventors: Kenji Sunagawa, Fukuoka (JP); Masaru Sugimachi, Osaka (JP); Takayuki Sato, Kochi (JP)

(73) Assignees: National Cerebral and Cardiovascular Center, Osaka (JP); Fujikin Inc., Osaka (JP)

( * ) Notice: Subject to any disclaimer, the term of this patent is extended or adjusted under 35 U.S.C. 154(b) by 0 days.

(21) Appl. No.: 13/030,200

(22) Filed: Feb. 18, 2011

(65) Prior Publication Data

US 2011/0144710 A1  Jun. 16, 2011

Related U.S. Application Data

(62) Division of application No. 12/103,786, filed on Apr. 16, 2008, which is a division of application No. 10/523,539, filed as application No. PCT/JP02/007963 on Aug. 5, 2002, now Pat. No. 7,835,791.

(51) Int. Cl.
*A61N 1/365* (2006.01)
(52) U.S. Cl. .......................................... 607/17
(58) Field of Classification Search ............... 607/17
See application file for complete search history.

(56) References Cited

U.S. PATENT DOCUMENTS

| 3,650,277 | A | 3/1972 | Sjostrand et al. |
| 4,006,351 | A | 2/1977 | Constant |
| 5,016,635 | A | 5/1991 | Graupe |
| 5,111,815 | A | 5/1992 | Mower |
| 5,199,428 | A | 4/1993 | Obel et al. |
| 5,423,325 | A | 6/1995 | Burton |
| 6,129,744 | A | 10/2000 | Boute |
| 6,223,078 | B1 | 4/2001 | Marcovecchio |
| 7,079,888 | B2 | 7/2006 | Oung et al. |
| 2002/0032469 | A1 | 3/2002 | Marcovecchio |
| 2006/0089678 | A1 | 4/2006 | Shalev |

FOREIGN PATENT DOCUMENTS

| CN | 1207948 | 2/1999 |
| EP | 0481583 A2 | 4/1992 |
| EP | 0688579 A1 | 12/1995 |
| JP | 5076609 | 3/1993 |

(Continued)

OTHER PUBLICATIONS

P.Z. Marmareliz, and V.Z. Marmareliz, "Analysis of Physiological Systems: the White Noise Approach," Plen. Pub., N. Y., 1978, pp. 18-29, 92-99, and 234-255.

(Continued)

*Primary Examiner* — Michael Kahelin
(74) *Attorney, Agent, or Firm* — Brown & Michaels, PC

(57) ABSTRACT

The present invention provides a cardiac pacing system based on biological activities, comprising: a) at least one nerve activity sensing means which senses nerve activity of a cardiac sympathetic nerve and/or a vagal nerve, and outputs a plurality of input nerve activity signals; b) a calculating means which receives the input nerve activity signals, calculates a transfer function by computing a Fourier transform of normal nerve activity signals and a normal heart rate signal from normal cardiovascular system, calculates an impulse response by computing an inverse Fourier transform of the transfer function, calculates a plurality of pacing signals for control of a heart rate using a convolution integral between the input nerve activity signals and the impulse response, and outputs the pacing signals; and c) a pacing means which receives the pacing signals, and stimulates the heart based on the pacing signals such that heart rate is regulated.

4 Claims, 8 Drawing Sheets

FOREIGN PATENT DOCUMENTS

| | | |
|---|---|---|
| JP | 10277165 | 10/1998 |
| JP | 2000014806 | 6/1999 |
| JP | 11514268 T | 12/1999 |
| RU | 2111771 C1 | 5/1998 |
| RU | 2155079 C2 | 8/1998 |
| WO | 9713550 A1 | 4/1997 |

OTHER PUBLICATIONS

International Preliminary Report on Patentability dated Nov. 11, 2004 for PCT/JP2002/007963.

International Search Report dated Nov. 26, 2002 for PCT/JP02/07963.

Fig. 3
(a) 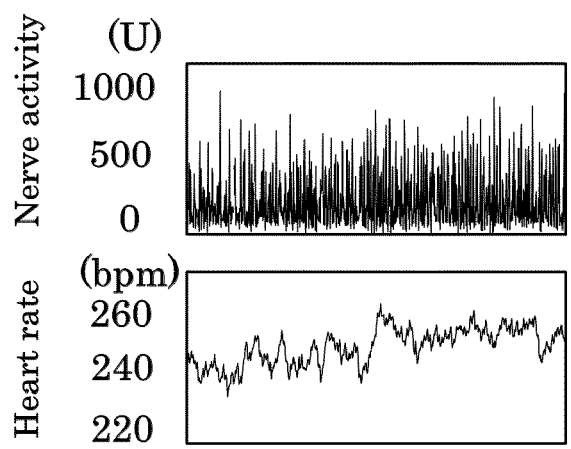
(b) 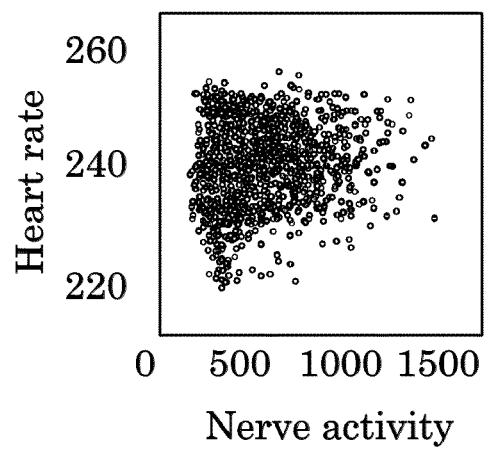
(c) 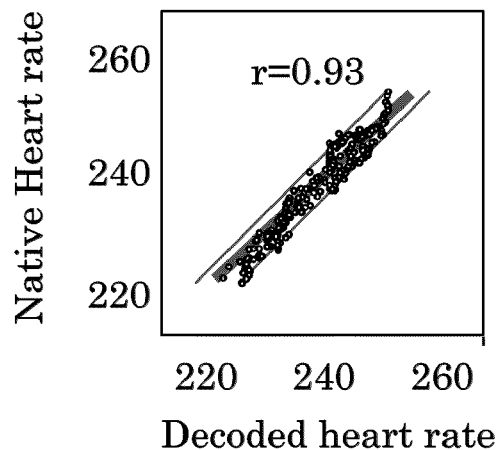

CARDIAC PACING SYSTEM BY SUBSTITUTING NATIVE BIOLOGICAL REGULATORY FUNCTION

REFERENCE TO RELATED APPLICATIONS

This is a divisional patent application of copending application Ser. No. 12/103,786, filed Apr. 16, 2008, entitled "CARDIAC PACING SYSTEM, BLOOD PRESSURE REGULATING SYSTEM, AND CARDIAC DISEASE TREATMENT SYSTEM BY SUBSTITUTING NATIVE BIOLOGICAL REGULATORY FUNCTION", which is a divisional application of application Ser. No. 10/523,539, now U.S. Pat. No. 7,835,791 filed Feb. 3, 2005, entitled "MEDICAL TREATMENT SYSTEM BY SUBSTITUTING NATIVE BIOLOGICAL REGULATORY FUNCTION; CARDIAC PACING SYSTEM, BLOOD PRESSURE REGULATING SYSTEM, AND CARDIAC DISEASE TREATMENT SYSTEM BASED ON THE MEDICAL TREATMENT SYSTEM", now U.S. Pat. No. 7,835,791, issued Nov. 16, 2010. The aforementioned applications are hereby incorporated herein by reference.

BACKGROUND OF THE INVENTION

1. Field of the Invention

The present invention is related to a cardiac pacing system, a blood pressure regulating system, and a cardiac disease treatment system by substituting native biological regulatory function. More particularly, the present invention provides a cardiac pacing system, a blood pressure regulating system, and a cardiac disease treatment system by substituting native biological regulatory function that is capable of regulating organs as if their central controllers were normally functioning even if the central controllers themselves become abnormal due to various causes.

2. Description of Related Art

Heart transplantation from brain dead subjects became legal in Japan to treat patients with severe heart failure. However, the number of heart donors is definitely small, and the shortage of hearts for transplantation has been seriously discussed worldwide.

An alternative treatment for patients with severe heart failure is artificial heart implantation. However, even the most recent artificial hearts are not regulated by native biological regulation, thereby they do not always operate in concert with native organs.

Pacemakers have been used for the treatment of patients with bradycardia. Pacemakers enable necessary rhythmic myocardial contraction by electrically stimulating the myocardium artificially.

Recently rate-responsive pacemakers have been developed, in which stimulation rate changes according to the estimated native heart rate from e.g., electrocardiographic QT time, body temperature, or body acceleration. However, specificity, sensitivity and transient response of heart rate regulation compared to native heart rate regulation by such pacemakers have not always been satisfactory.

In some other diseases, it is well known that abnormal native regulatory function promotes disease processes. For example, it is known that abnormal native regulatory mechanisms participate in the progression of heart disease, and it is well known that sympathetic nerve overactivation and abnormal vagal nerve withdrawal occur after the onset of acute myocardial infarction, and worsens the outcome.

Such abnormal native regulatory function can also be observed in circulatory diseases other than heart diseases.

Even in normal subjects, 300 to 800 mL of blood shifts to the lower extremities and internal organs below the heart level during standing, causing decreased venous return to the heart and hypotension. Normal subjects usually have a blood pressure regulating mechanism to counteract this and to maintain a constant blood pressure, thereby preventing orthostatic hypotension. Subjects with various disorders and a damaged blood pressure regulating system, however, suffer from orthostatic hypotension. For example, in patients with Shy-Drager syndrome, a part of the nervous system involved in blood pressure regulation becomes abnormal, and quality of life is seriously impaired due to large fluctuations in blood pressure with their body position change.

Artificial organs and artificial devices, such as conventional artificial hearts and cardiac pacemakers, do not always operate in concert with native organs, as described above, because they are not intended to be controlled by the native regulatory system. Therefore their performance, in terms of sensitivity to changes in the native organs, is not satisfactory.

Pharmacological treatment with drugs such as coronary vasodilators, B-adrenergic blockers and anti-platelet agents, catheter-based interventional treatment, and coronary artery bypass surgery have been developed as treatments for myocardial infarction.

However, even when taking full advantage of all of the pharmacological, interventional and surgical treatments available, progression of pathology even to death is often inevitable.

Adrenergic agonists, such as epinephrine, levodopa and amphetamine, are used for pharmacological treatment of Shy-Drager syndrome with severe orthostatic hypertension, and excessive salt is administered for symptomatic relief. Although symptoms can be alleviated to some extent, it is impossible to treat Shy-Drager syndrome and restore full function.

The present invention provides a cardiac pacing system, a blood pressure regulating system, and a cardiac disease treatment system that are capable of regulating organs as if their central controllers were normally functioning even if the central controllers themselves become abnormal by various causes.

SUMMARY OF THE INVENTION

A cardiac pacing system based on biological activities includes a nerve activity sensing means which senses nerve activities of the cardiac sympathetic nerve and/or the vagal nerve, and outputs nerve activity signals. A calculating means receives the nerve activity signals sensed by the nerve activity sensing means, analyzes and processes the nerve activity signals to calculate pacing signals to control the heart rate, and outputs the pacing signals. A pacing means receives the pacing signals, and stimulates the heart on the basis of the pacing signals to regulate heart rate.

A blood pressure regulating system, which uses the native regulation rule to estimate nerve activities in response to blood pressure changes, includes a blood pressure sensing means, which senses blood pressure and outputs a blood pressure signal. A calculating means receives the blood pressure signal sensed by the blood pressure sensing means, analyzes and processes the blood pressure signal to calculate a sympathetic nerve stimulation signal for the regulation of blood pressure by the stimulation of sympathetic nerve innervating vascular beds, and outputs the sympathetic nerve stimulation signal. A nerve stimulating means receives the sympathetic nerve stimulation signal calculated by the calculating means, and stimulates the sympathetic nerve innervating vascular beds on the basis of the sympathetic nerve stimulation signal to regulate blood pressure.

A system to treat cardiac diseases includes a cardiovascular activity sensing means which senses cardiovascular activity information issued by the cardiovascular system, and outputs cardiovascular activity signals. A calculating means receives the cardiovascular activity signals sensed by the cardiovascular activity sensing means, analyzes and processes the cardiovascular activity signals to calculate nerve stimulation signals, and outputs the nerve simulation signals. A nerve stimulating means receives the nerve stimulation signals, and stimulates the nerve on the basis of the nerve stimulation signals.

BRIEF DESCRIPTION OF THE DRAWINGS

FIG. 3(a) shows the changes in sympathetic nerve activity and heart rate with time.

FIG. 3(b) is a scatter plot showing the relationship between sympathetic nerve activity and simultaneous heart rate, obtained by data shown in FIG. 3(a).

FIG. 3(c) is a scatter plot between the predicted heart rate obtained from sympathetic nerve activity and impulse response, i.e., the required heart rate by organisms, on one hand, and the measured heart rate on the other.

DETAILED DESCRIPTION OF THE INVENTION

Figure 1:
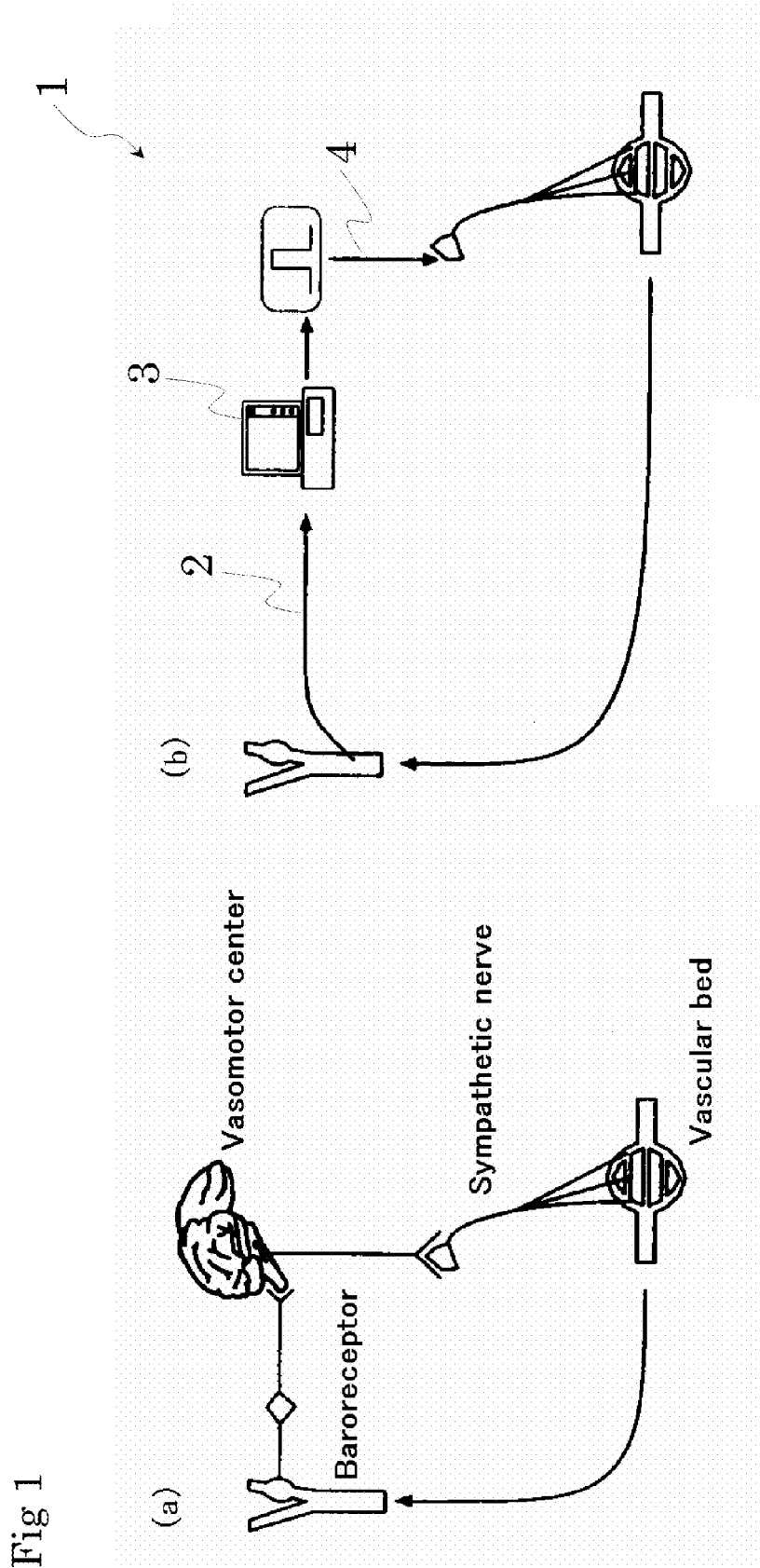
FIG. 1(a) is a schematic illustration showing the components of a native normally functioning baroreflex.
FIG. 1(b) is a schematic illustration showing how to apply the device used for the present invention to native abnormally functioning baroreflex.

The device to treat diseases used for the present invention is capable of restoring native regulatory function as if the lost or abnormal native regulatory functions became normally functioning by substituting the lost or abnormal native functions with the device. As an example, the device is explained by describing an application of the invention to blood pressure regulation in detail. FIG. 1(a) is a schematic illustration showing the components of a native baroreflex or blood pressure regulation system. Information about the changes in blood pressure is transmitted from baroreceptors to the solitary tract nucleus in the medulla oblongata. The solitary tract nucleus then in turn changes sympathetic nerve activity to regulate blood pressure by e.g., vasoconstriction. FIG. 1(b) is a schematic illustration where the device (1) used for the present invention was applied to maintain normal blood pressure regulation even when the native vasomotor center fails to achieve normal function by various causes. Blood pressure can be maintained in a normal way by sensing blood pressure with a blood pressure sensing means (2), by converting the blood pressure signal into the signal for nerve stimulation with a nerve stimulating means (4) by a calculating means (3), and by stimulating the nerve with the nerve stimulating means (4) according to the calculated signals.

Figure 2:
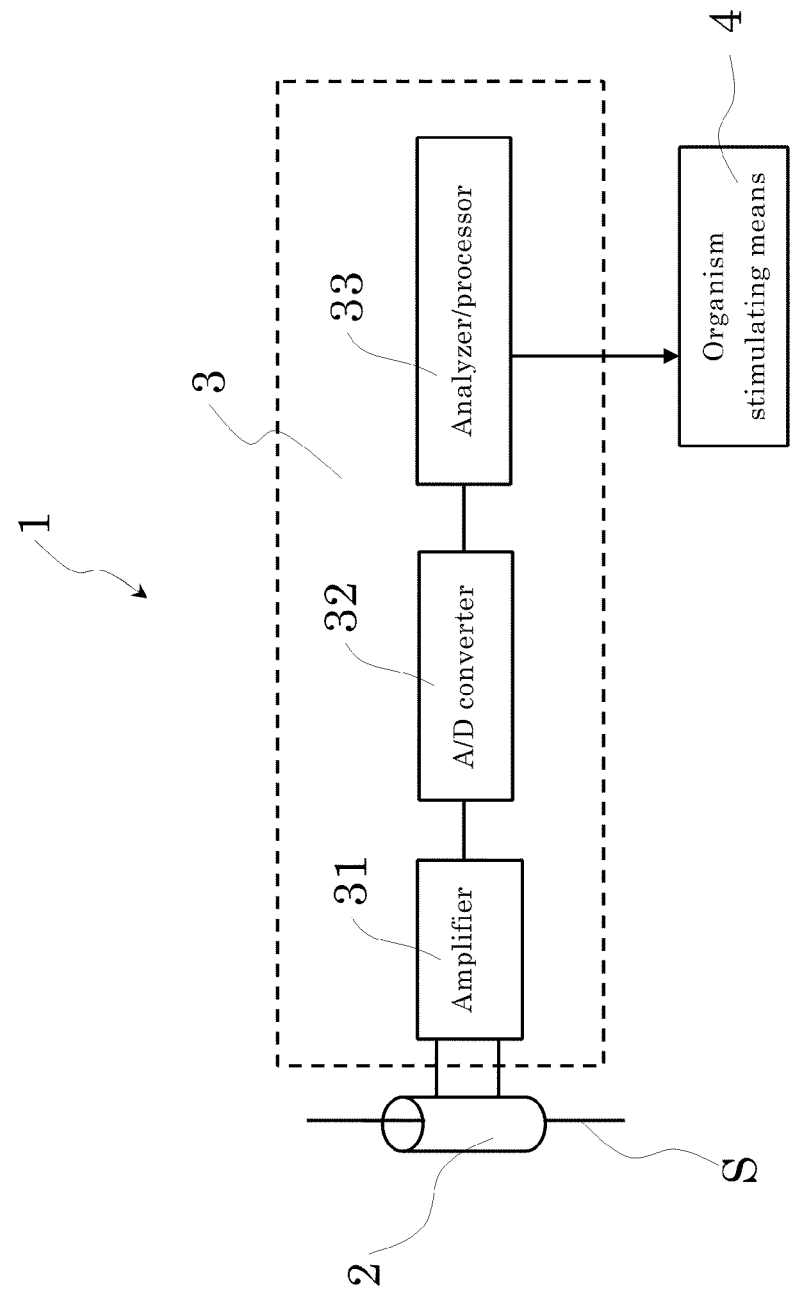
FIG. 2 is a block diagram depicting the outline of the device used for the present invention.

The device to treat diseases used for the present invention is described in more detail in the following paragraphs with reference to the figures. FIG. 2 is a block diagram depicting an outline of the device used for the present invention. The disease treatment device (1) disclosed herein includes at least a biological activity sensing means (2), a calculating means (3), and an organism stimulating means (4).

The biological activity sensing means (2) can output biosignals to the calculating means (3) by sensing biological activity information issued by biological activities of organisms (S). Some examples of the biological activity sensing means (2) include, but are not limited to, electrodes and pressure sensors.

Biosignals sensed by the biological activity sensing means (2) include, but are not limited to, sympathetic nerve activities and parasympathetic nerve activities, blood flow, blood pressure, body temperature, electrocardiogram, electroenchephalogram, and various biochemical markers. One can choose any necessary biosignals that are required for the device to achieve the purpose.

The number of the biological activity sensing means (2) of the device is not limited. Although only one biological activity sensing means (2) is shown in FIG. 2, two or more biological activity sensing means may be supplied to meet the requirements of the device. If there are multiple biological activity sensing means in the device, they may be located at the same site or at different sites within the organism.

The calculating means (3) can analyze and process biosignals sensed by the biological activity sensing means (2) and transferred to the calculating means, to calculate the signals to stimulate the organism. The calculated signals are transferred to the organism stimulation means (4).

More specifically, the biosignals sensed by the biological activity sensing means (2) are fed into amplifiers (31) in the calculating means (3) for signal amplification. These amplifiers (31) preferably include filters (not shown) capable of eliminating unnecessary higher or lower frequency biosignals or power line noises. The amplified signals are converted from analog to digital signals with the aid of analog-to-digital (A/D) converters (32), and then transferred to analyzers/processors (33). The analyzers/processors (33) process data to calculate signals to be transferred to organism stimulating means (4).

To explain how the calculating means (3) analyzes and processes biosignals, an example of regulating heart rate is provided. FIG. 3 is a graph showing the relationship between sympathetic nerve activity and heart rate of a representative rabbit. FIG. 3(a) is a graph showing simultaneously measured changes in cardiac sympathetic nerve activity and heart rate with time. Although, as shown in FIG. 3(a), there is a tendency for the heart rate to increase with an increase in cardiac sympathetic nerve activity, the correlation between nerve activity and simultaneous heart rate is poor (see FIG. 3(b)). Therefore, it is impossible to regulate heart rate using sympathetic nerve activity itself.

With an impulse response function of heart rate in response to sympathetic nerve activity, however, it is possible to estimate heart rate, which is considered to follow the requirements of organisms. FIG. 3(c) is a scatter plot between the heart rate estimated from impulse response function and measured sympathetic nerve activity on one hand, and measured heart rate on the other. As shown in this figure, measured and estimated heart rate correlated well (correlation function 0.93).

Therefore, by analyzing and processing nerve activity signals by the calculating means (3), the heart rate actually required by organisms can be obtained. In the above example, one can regulate heart rate by stimulating the heart electrically according to the estimated heart rate, as if it were regulated by the normal central nervous system.

In addition to the above-described example for heart rate regulation, similar related explanations are possible for other various native regulations that are essential for the maintenance of biological functions, such as blood pressure regulation.

Discriminating means (not shown), judging whether biosignals coming into the calculating means (3) arise from normal biological activities or from abnormal biological activities, may also optionally be provided in the calculating means (3). To discriminate between input biosignals from normal biological activities and input biosignals from abnormal biological activities, information about normal-activity biosignals are stored in memory means (not shown), and the input biosignals are compared with the stored information. When the difference exceeds a previously determined threshold for a given time period, the signals are judged to be abnormal-activity signals.

When the discriminating means is provided, the calculating means does not output signals to the organism stimulating means for input of normal-activity biosignals, and the native regulatory system itself works. On the other hand, for abnormal-activity biosignals, the device works so that the signals to stimulate the organism are prepared for the organism stimulating means by analyzing and processing biosignals to correct the abnormal biological activity. In other words, for inputs of normal biological activities, the device needs to perform no action to maintain normal activities. For inputs of abnormal biological activities, the device outputs signals to correct abnormal biological activities to normal biological activities.

When more than one biological activity sensing means are provided, the analysis and processing described above are performed for each respective biological activity sensing means.

The organism stimulating means (4) receives the signals to stimulate the organism from the calculating means (3), and stimulates the organism based on the signals. Examples of stimulation by the organism stimulating means (4) may include, but are not limited to, electrical stimulation of nerves, myocardium, cerebrum and cerebellum, stimulation with the use of devices for drug administration, artificial pancreas, artificial hearts, and artificial ventilators.

The following section explains the device to treat diseases used for the present invention in detail with reference to more specific examples. First, the cardiac pacing system, the first embodiment of the present invention, is described.

The basic structure of the cardiac pacing system according to the first embodiment is the same as the device (1) shown in FIG. 2. The cardiac pacing system includes at least the biological activity (in this case, nerve activity) sensing means (2), the calculating means (3) and the organism stimulating (in this case, cardiac pacing) means (4).

The biological activity (nerve activity) sensing means (2) senses the nerve activity of the cardiac sympathetic nerve and/or the vagal nerve, and outputs nerve activity signals.

The biological activity (nerve activity) sensing means (2) are preferably installed in both the cardiac sympathetic nerve and the vagal nerve in order to sense both the activities of the cardiac sympathetic nerve and the vagus nerve. This is because it is known that regulation of heart rate is usually related to both the cardiac sympathetic nerve and the vagal nerve. Installing the sensing devices in both the cardiac sympathetic nerve and the vagal nerve enables heart rate to be regulated to be less when the vagal activity is enhanced, and to be regulated to be more when the sympathetic activity is enhanced. In other words, since the heart is regulated by the two nerve systems, it is difficult to regulate heart rate to an arbitrary target by only one nerve system.

Although it is preferable in this embodiment to provide two biological activity (nerve activity) sensing means (2) as described above, any one of the means may be provided depending on the purpose of the system.

The biological activity (nerve activity) sensing means (2) is exemplified by an electrode but is not limited thereto so long as it is able to sense the nerve activity and output the nerve activity signals.

The calculating means (3) receives the nerve activity signals sensed by the nerve activity sensing means (2), analyzes and processes the nerve activity signals, and calculates and outputs pacing signals for regulating heart rate.

The nerve activity signals sensed by the nerve activity sensing means (2) and the simultaneously measured heart rate are not correlated in a one-to-one manner. Therefore, it is necessary to calculate the pacing signals for regulating heart rate from the nerve activity signals by the calculating means (3).

To calculate the pacing signals for regulating heart rate from the nerve activity signals, one can use, for example, the impulse response of changes in heart rate in response to changes in nerve activity.

The pacing signals derived from the calculating means (3) are fed into the organism stimulating (pacing) means (4). The organism stimulating (pacing) means stimulates the heart based on the pacing signals to regulate heart rate.

The organism stimulating (pacing) means (4) is exemplified by a cardiac pacemaker but not limited thereto so long as it can regulate heart rate by stimulating the heart based on the pacing signals.

As described in detail above, the cardiac pacing system according to the present invention is based on the nerve activities of the cardiac sympathetic nerve and/or vagal nerve, but does not use the nerve activities themselves as the pacing signals. The system instead paces the heart based on the pacing signals with heart rate estimated from the nerve activities. Therefore, the system is excellent in specificity, sensitivity and transient response.

Next, the blood pressure regulating system, a second embodiment of the present invention, is explained.

The basic structure of the blood pressure regulating system according to the second embodiment is the same as the device (1) shown in FIG. 2. The blood pressure regulating system includes at least the biological activity (in this case, blood pressure) sensing means (2), the calculating means (3) and the organism (in this case, nerve) stimulating means (4).

The biological activity (blood pressure) sensing means (2) senses blood pressure, and outputs the blood pressure signal. The biological activity (blood pressure) sensing means (2) is exemplified as a pressure sensor but is not limited thereto so long as it can output the blood pressure signal by sensing blood pressure.

Baroreceptors distributed in the carotid sinus and aortic arch sense extension of arterial walls with increases in blood pressure, and cause increased impulse transmission to the solitary tract nucleus of the medulla oblongata. In response to this, the solitary tract nucleus suppresses sympathetic nerve activity and stimulates parasympathetic nerve activity. In contrast, when blood pressure drops, stimulation of baroreceptors decreases, the solitary tract nucleus is suppressed, parasympathetic nerve activity is suppressed, and sympathetic nerve activity is stimulated. These, in turn, increase heart rate and cause peripheral vasoconstriction and blood pressure is maintained. Veins also contract to increase venous return to the heart.

The blood pressure regulating system can be used for patients who are unable to maintain normal blood pressure due to failures in the blood pressure regulating system.

The calculating means (3) receives the blood pressure signals sensed by the biological activity (blood pressure) sensing means (2), analyzes the blood pressure signals, calculates signals to stimulate the sympathetic nerve that can regulate blood pressure by stimulating the sympathetic nerve innervating vascular beds, and outputs the calculated signals to stimulate the sympathetic nerve.

Similar to heart rate regulation, the blood pressure signals sensed by the biological activity (blood pressure) sensing means (2) and the sympathetic nerve activity signals are not correlated in a one-to-one manner in blood pressure regulation. Therefore, it is necessary to calculate the signals to stimulate sympathetic nerve innervating vascular beds for blood pressure regulation from blood pressure signals by the calculating means (2).

To calculate the signals to stimulate the sympathetic nerve innervating vascular beds for blood pressure regulation, one can use, for example, the impulse response of changes in sympathetic nerve activity in response to changes in blood pressure. These may be used to calculate the signals to stimulate the sympathetic nerve that can regulate the blood pressure.

The organism (nerve) stimulating means (4) receives the signals to stimulate the sympathetic nerve calculated by the calculating means (3), and regulates blood pressure by stimulating the sympathetic nerve innervating vascular beds based on those signals. The sympathetic nerve stimulating sites are exemplified by sympathetic ganglia, surface of the spinal cord, and preferred sites in the brain, but are not limited thereto so long as they can stimulate the sympathetic nerve.

As described in detail above, the blood pressure regulating system according to the present invention is based on blood pressure, but does not use blood pressure itself as the signals to stimulate the sympathetic nerve. The system instead stimulates the sympathetic nerve based on the signals to stimulate the sympathetic nerve estimated from the blood pressure. Therefore, the system can perform stable blood pressure regulation as native pressure regulation.

A third embodiment of the present invention is a cardiac disease treating system.

The basic structure of the cardiac disease treating system is the same as the device (1) shown in FIG. 2. The cardiac disease treating system includes at least the biological activity (in this case, cardiac activity) sensing means (2), the calculating means (3) and the organism (in this case, nerve) stimulating means (4).

The cardiac disease treating system is effective for correcting the cardiac function, which has become abnormal due to any one of a number of various diseases. For example, it is known that abnormal native regulation is involved in the progression of cardiac diseases, and abnormal sympathetic overactivities and vagal withdrawal have been shown with myocardial infarction. It is possible to prevent the progression of various diseases by correcting the abnormal native functional state with the system according to the present invention.

In the cardiac disease treating system, the biological activity (cardiac activity) sensing means (2) senses cardiac activity information issued by native cardiac activity and outputs cardiac activity signals. Cardiac activity information sensed by the biological activity (cardiac activity) sensing means (2) is exemplified by heart rate and electrocardiogram information.

The calculating means (3) receives cardiac activity signals sensed by the biological activity (cardiac activity) sensing means (2), analyzes and processes the cardiac activity signals, calculates signals to stimulate the nerve that can regulate cardiac activities by stimulating nerves, and outputs the signals to stimulate the nerve.

Before patients get ill, the native regulatory mechanism is normally operating in patients to whom the cardiac disease treating system according to the present invention may be applied. Once falling ill due to any one of a number of various cardiac diseases, however, the native regulatory mechanism does not help the patient recover.

In the cardiac disease treating system, the calculating means (3) includes a discriminating means (not shown) to discriminate between cardiac activity information fed into the calculating means (3) that arises from normal biological activities and cardiac activity information from abnormal biological activities. In this manner, the calculating means does not calculate signals to stimulate nerve stimulating signals and does not output the signals to stimulate the nerve to the organism (nerve) stimulating means (4) when it is determined that the heart is functioning normally by inputting cardiac activity information sensed by the biological (cardiac) activity sensing means (2). In this situation, the organism is regulated by its native regulatory mechanism. When it is determined that the heart is abnormally functioning by inputting cardiac activity information sensed by the biological activity (cardiac activity) sensing means (2), on the other hand, the calculating means calculates the nerve stimulating signals to correct the abnormal function of the heart, and outputs the signals to the organism (nerve) stimulating means (4).

The signals to stimulate the nerve derived from the calculating means (3) are fed into the organism (nerve) stimulating means (4). The organism (nerve) stimulating means (4) stimulates the nerve based on the signals to stimulate the nerve and to regulate cardiac activities.

The organism (nerve) stimulating means (4) is exemplified by an electrode, but is not limited thereto so long as it is able to regulate cardiac activities by stimulating the nerve based on the signals to stimulate the nerve. Nerve stimulating sites are exemplified by the vagal nerve, the aortic depressor nerve, and preferred sites in the brain, but are not limited thereto so long as they are able to regulate cardiac activities.

Although the present invention is explained in detail with reference to the following examples, the present invention is not limited to these examples.

Example 1

The anterior descending branch of the left coronary artery in 20 anesthetized rats was ligated to create rats with myocardial infarction. Mortality was periodically tabulated in this group.

In 16 other rats with myocardial infarction, heart rate was decreased by stimulating the vagal nerve (pulse width: 2 msec, pulse voltage: 2 V, pulse frequency: 2 Hz) from 2 minutes after the onset of myocardial infarction. Mortality was also periodically tabulated in this group.

In 15 additional rats with myocardial infarction, heart rate was decreased by stimulating the vagal nerve (pulse width: 2 msec, pulse voltage: 2 V, pulse frequency: 5 Hz) from 2 minutes after the onset of myocardial infarction. Mortality was periodically tabulated in this group.

Figure 4:
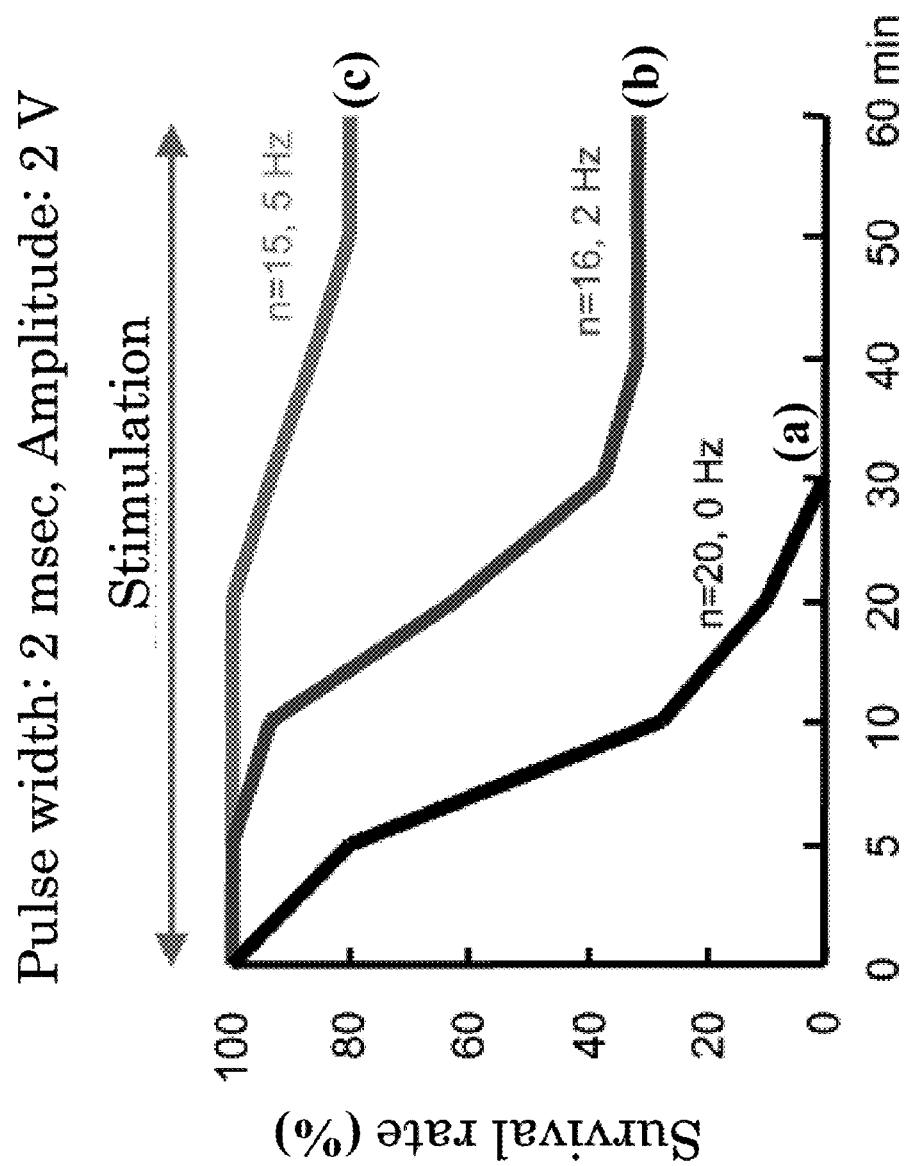
FIG. 4 is a graph showing results obtained in Example 1.

The mortality results are shown in FIG. 4.

The results in this example show that all rats with myocardial infarction but with no treatment by vagal stimulation died within 30 minutes (FIG. 4(a)). On the other hand, mortality after 60 minutes from the onset of the test was decreased to about 60% when the vagal nerve was stimulated with a pulse frequency of 2 Hz (FIG. 4(b)). Mortality after 60 minutes was further decreased to about 20% when the vagal nerve was stimulated with a pulse frequency of 5 Hz (FIG. 4(c)).

These results indicate that stimulating the vagal nerve is effective in the treatment of myocardial infarction soon after its onset.

Example 2

Since Example 1 was performed under anesthesia, the following test was performed to exclude the effects of anesthesia.

Blood pressure telemeter, vagal nerve tele-stimulating device and coronary artery cuff occluders to create myocardial infarction were implanted in 32 rats.

When the rats had fully recovered from surgery for one week, the descending anterior branch of the left coronary artery was occluded with the use of cuff occluders in 12 out of 32 rats. Mortality was tabulated periodically with no vagal nerve stimulation.

In another 10 out of the 32 rats, the vagal nerve was stimulated (pulse width: 0.2 msec, pulse current: 0.1 mA, pulse frequency: 20 Hz) immediately after the occlusion of the coronary artery with cuff occluders for 60 minutes. Mortality was tabulated periodically with vagal nerve stimulation.

In another 10 out of the 32 rats, the vagal nerve was stimulated (pulse width: 0.2 msec, pulse current: 0.2 mA, pulse frequency: 20 Hz) immediately after the occlusion of the coronary artery with cuff occluders for 60 minutes. Vagal nerve stimulation was performed with local anesthetic application proximal to the stimulation site to prevent afferent vagal stimulation to the cerebrum (to prevent rats from being restless with the stimulation of 0.2 mA). Mortality was tabulated periodically with vagal nerve stimulation.

Figure 5:
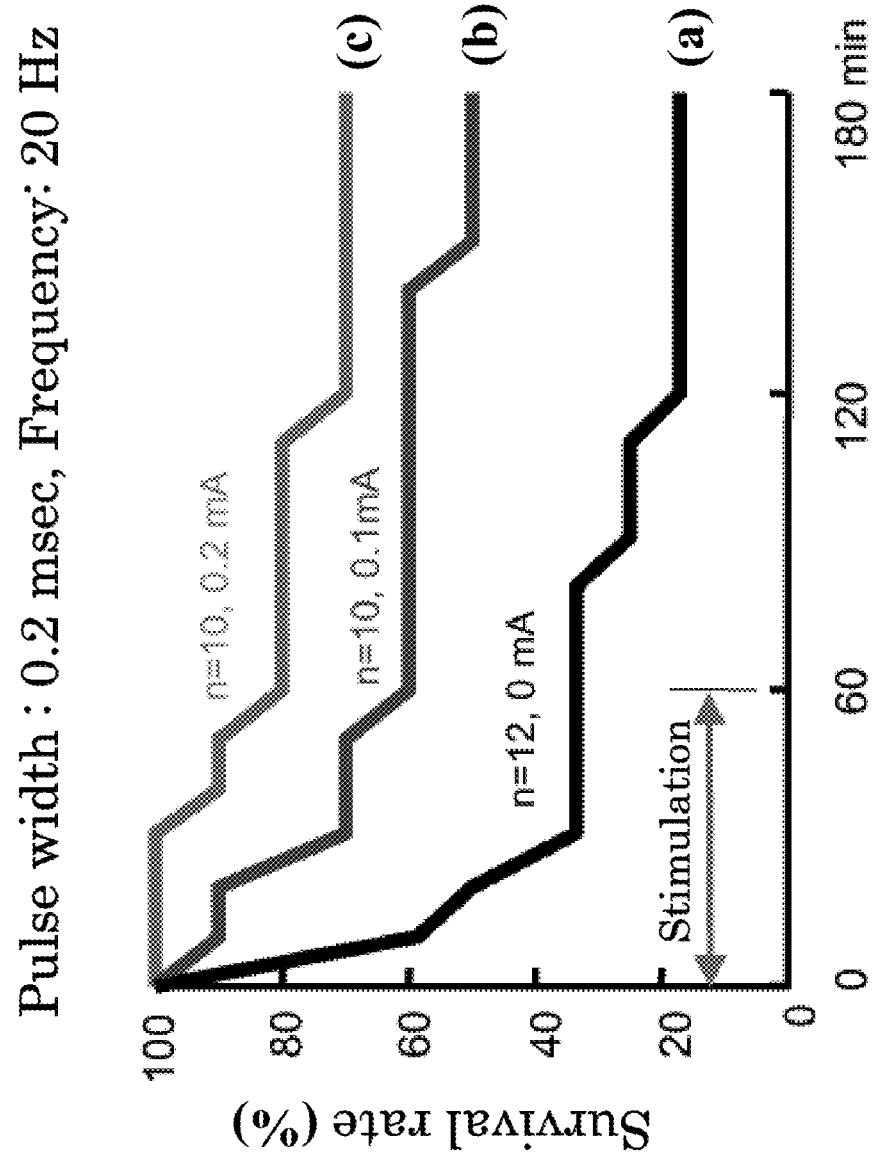
FIG. 5 is a graph showing results obtained in Example 2.

The mortality results are shown in FIG. 5.

As shown in FIG. 5, 66% of the rats died within 60 minutes after the coronary occlusion with no vagal stimulation (FIG. 5 (a)). On the other hand, mortality was limited to 40% when the heart rate was decreased by 20 beats per minute by vagal stimulation of 0.1 mA (FIG. 5(b)). Furthermore, with vagal stimulation of 0.2 mA, mortality was further limited to 20% (FIG. 5 (c)).

After additional observation for 2 hours, i.e. at 3 hours after the onset of the test, mortality was 83% with no vagal stimulation, 50% with vagal stimulation of 0.1 mA, and 30% with vagal stimulation of 0.2 mA, expanding the disparity between the three groups of rats.

The above results indicate that reduction of mortality immediately after myocardial infarction is possible by correcting the abnormal regulatory function with vagal stimulation, irrespective of the presence or the absence of anesthesia.

Example 3

The following tests were performed to investigate the long-term effects.

Myocardial infarction was created under anesthesia in the same manner as in Example 1. Surviving rats after every attempt of resuscitation (survival rate after 1 week being ~40%) underwent another surgery 1 week after the first surgery. Blood pressure telemeter, vagal nerve tele-stimulating device and coronary artery cuff occluders to create myocardial infarction were implanted in these rats in the same manner as in Example 2.

After an additional 1 week, in half of the rats (13 rats), vagal stimulation was started with the stimulation condition to decrease the heart rate by 20 beats (pulse width: 0.2 msec, pulse current: 0.1 to 0.13 mA, pulse frequency: 20 Hz), and the vagal nerve was stimulated for 10 seconds every 1 minute. The test was continued for 5 weeks. No vagal stimulation was applied to the remaining half of the rats (13 rats). No rat deaths were observed in 5 weeks.

Figure 6:
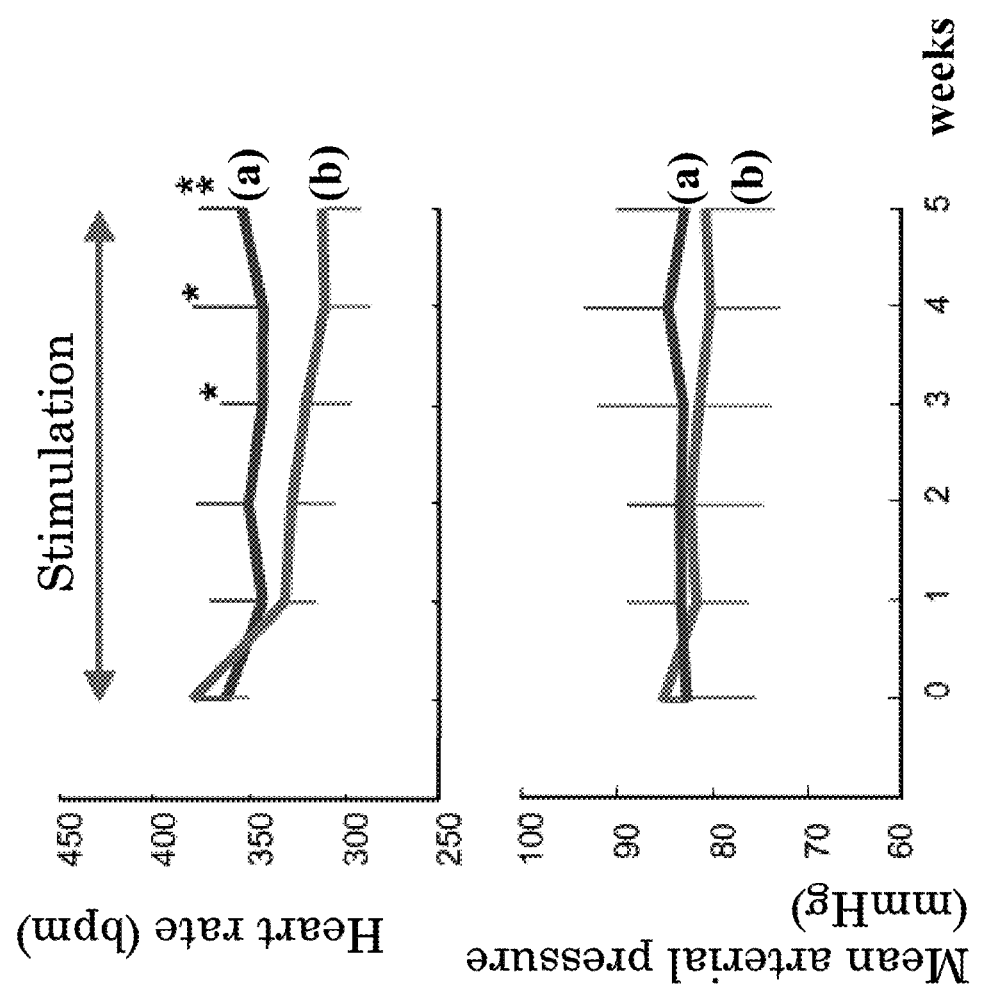
FIG. 6 is a graph showing results obtained in Example 3.

Changes in blood pressure and heart rate were measured throughout the test period. The results are shown in FIG. 6. FIG. 6(a) shows the results for the rats with no vagal stimulation, and FIG. 6(b) shows the results for the rats with vagal stimulation.

As shown in FIG. 6, heart rate progressively decreased with vagal stimulation, but blood pressure did not change significantly with vagal stimulation.

At 5 weeks, the ventricular weight of the rats was measured. The results are shown in Table 1.

TABLE 1

| weight | Biventricular weight | Left ventricular weight | (per 1 kg of body weight) Right ventricular weight |
|---|---|---|---|
| With vagal stimulation | 2.71 ± 0.24 g | 1.86 ± 0.12 g | 0.85 ± 0.27 g |
| Without vagal stimulation | 3.01 ± 0.31 g | 2.03 ± 0.18 g | 0.98 ± 0.30 g |

As shown in Table 1, ventricular weight was significantly smaller in rats with vagal stimulation, indicating ventricular remodeling after myocardial infarction was suppressed. Since ventricular remodeling is known to correlate with mortality in the chronic phase of myocardial infarction, the above results indicate that vagal stimulation enables the correction of the abnormal regulatory mechanism, resulting in a decrease in long-term mortality.

Example 4

The following tests were performed to investigate the effect of vagal stimulation on the long-term mortality.

Myocardial infarction was created under anesthesia in the same manner as in Example 1. Surviving rats after every attempt of resuscitation (survival rate after 1 week being ~40%) underwent another surgery 1 week after the first surgery. Blood pressure telemeter, vagal nerve tele-stimulating device and coronary artery cuff occluders to create myocardial infarction were implanted in these rats in the same manner as in Example 2. After an additional 1 week, in half of the rats (22 rats), vagal stimulation was started with the stimulation condition to decrease heart rate by 20 beats (pulse width: 0.2 msec, pulse current: 0.1 to 0.13 mA, pulse frequency: 20 Hz), and the vagal nerve was stimulated for 10 seconds every minute for 40 days. The test was continued for 180 days. No vagal stimulation was applied to the remaining half of the rats (23 rats).

Figure 7:
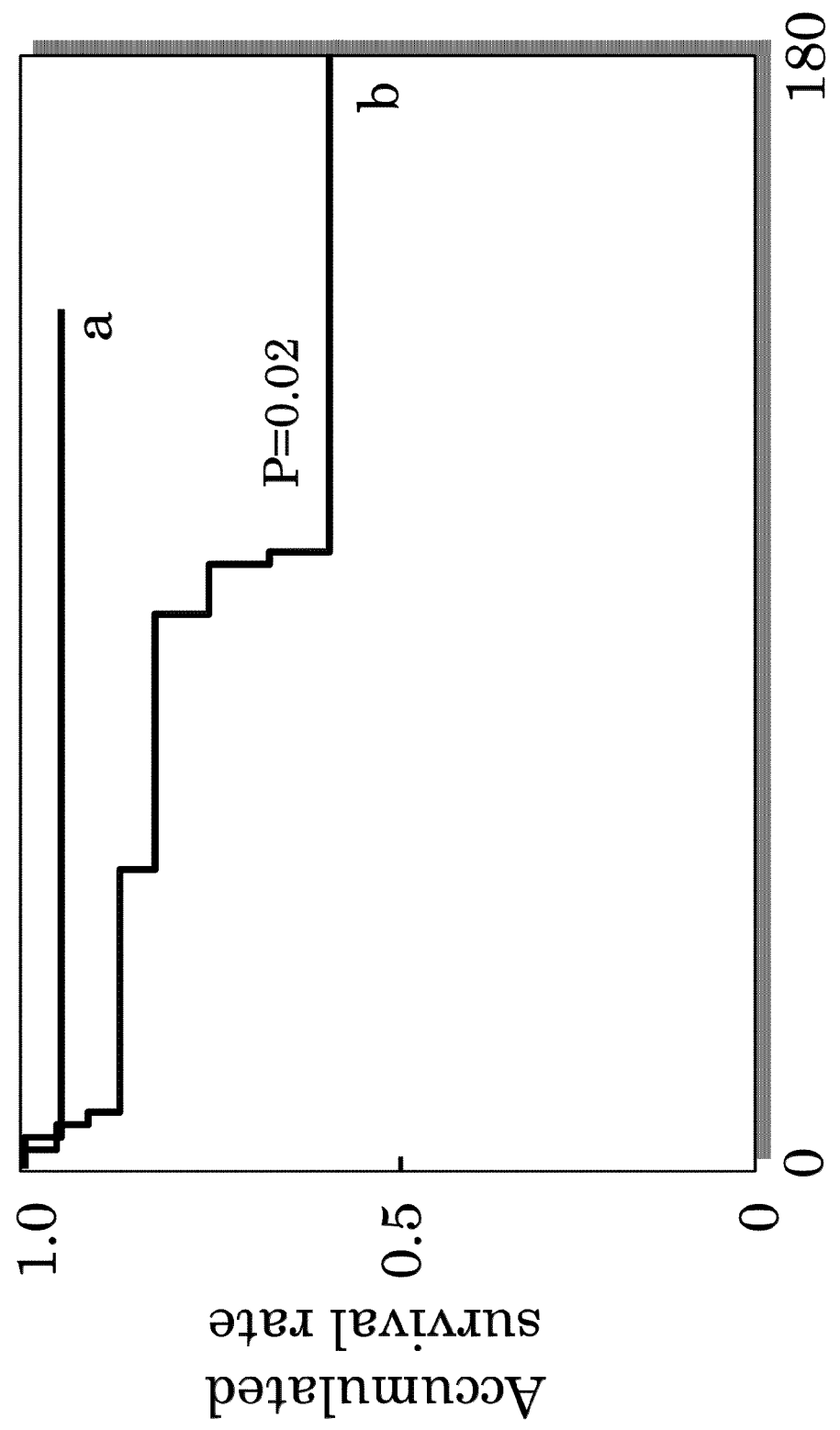
FIG. 7 is a graph showing results obtained in Example 4.

As shown in FIG. 7 by accumulated survival ratio during the test, 8 out of the 23 rats died, resulting in the final accumulated survival ratio of 0.57 (FIG. 7(a)). In contrast, only 1 out of the 22 rats with vagal stimulation of 0.1 to 0.13 mA died, resulting in a final accumulated survival ratio of 0.95 (FIG. 7(b)).

The above results indicate that the abnormal regulatory mechanism was corrected by vagal stimulation, and long-term mortality after myocardial infarction can be reduced.

Example 5

In anesthetized Japanese white rabbits, the impulse response function of heart rate in response to cardiac sympathetic nerve activity was obtained from measured heart rate and cardiac sympathetic nerve activity. Since heart rate fluctuation is not large enough in anesthetized animals compared to conscious animals, heart rate was artificially altered by randomly changing pressure imposed on baroreceptors.

Eight Japanese white rabbits were sedated and anesthetized. Pancuronium bromide and heparin sodium were intravenously injected to eliminate contaminated muscular activities and to prevent blood coagulation, respectively.

Bilateral carotid arteries, aortic depressor nerves, and vagal nerves were exposed by neck incision in rabbits. Bilateral carotid arteries were cannulated with silicone rubber tubes connected to a servo-controlled piston pump. Carotid sinus pressure was randomly changed by applying a band-limited white noise to the servo-pump. To avoid the effect of other baroreflex systems such as those arising from aortic arch baroreceptor and cardiopulmonary baroreceptor, bilateral vagal nerves and bilateral aortic depressor nerves were cut. After thoracotomy, the left cardiac sympathetic nerve was separated and cut. To measure cardiac sympathetic nerve activity (SNA), a pair of platinum electrodes was attached at the proximal end. Carotid sinus pressure and aortic pressure were also measured. Atrial electrocardiogram was measured by attaching electrodes to the left atrial appendage. Atrial electrocardiogram was fed into a tachometer to measure instantaneous heart rate (HR). Measured heart rate and cardiac sympathetic nerve activity are exemplified in FIG. 3(a).

Time series of cardiac sympathetic nerve activity and heart rate were divided into segments. Each segment was subjected to Fourier transform to determine power of sympathetic nerve activity ($S_{SNA\text{-}SNA}(f)$), power of heart rate ($S_{HR\text{-}HR}(f)$), and cross-power between sympathetic nerve activity and heart rate ($S_{HR\text{-}SNA}(f)$), then transfer function (H(f)) was calculated based on the following equation (Equation 1). Impulse response (h(t)) was determined by the inverse Fourier transform of the transfer function.

$$H(f) = \frac{S_{HR-SNA}(f)}{S_{SNA-SNA}(f)} \quad (1)$$

How accurately heart rate can be predicted from cardiac sympathetic nerve activity with the impulse response obtained by the above procedure was tested.

Sympathetic nerve activity and heart rate were measured similarly to the above described method. Heart rate was predicted from sympathetic nerve activity using a convolution integral between the above-obtained impulse response and the measured sympathetic nerve activity (Equation 2).

$$HR(t) = \sum_{\tau=1}^{N} h(\tau) \cdot SNA(t-\tau) \quad (2)$$

(where N is the length of impulse response, t is time and $\tau$ is a convolution integral parameter, and all signals were discretized at every 0.2 s.)

The correlation coefficient between measured and predicted heart rate was calculated to be as high as 0.80 to 0.96 (median: 0.88), and the error between measured and predicted heart rate was 1.4 to 6.6 beats/minutes (median: 3.1 beats/minutes), which was as small as 1.2±0.7% of the average heart rate.

From the above results, one can conclude that heart rate can be accurately predicted from cardiac sympathetic nerve activity.

Example 6

The rule or the logic how the native blood pressure regulatory center (vasomotor center) determines the sympathetic nerve activity in response to blood pressure information was obtained in 10 rats. For this, baroreceptors of animals were isolated from the rest of the circulation, and changes in blood pressure caused by the regulatory function of vasomotor center in response to changes in pressure imposed on baroreceptors were measured. Open-loop transfer function ($H_{native}$) of baroreflex system was determined from the relation between the input (pressure on baroreceptors) and output (blood pressure). Next, changes in blood pressure in response to changes in sympathetic nerve stimulation were measured. Transfer function ($H_{STM \to SAP}$) from sympathetic nerve activity (STM) to blood pressure (SAP) was determined from these data. Transfer function ($H_{BRP \to STM}$) of the vasomotor center, which characterizes the changes in sympathetic nerve activity (STM) in response to pressure on baroreceptors (BRP), was determined as $H_{native}/H_{STM \to SAP}$.

Ten rats were anesthetized and intratracheal tubes were inserted through the mouth for artificial ventilation. Pancuronium bromide was intravenously injected to eliminate contaminating muscular activities. Arterial blood gas was monitored with a blood gas measurement device. A polyethylene tube was inserted into the right femoral vein and physiological saline was infused to avoid dehydration. A micromanometer-tipped catheter was inserted into the aortic arch via the right femoral artery.

Bilateral carotid sinuses were isolated from the rest of the circulation to open the baroreflex feedback loop, and vagal nerves and aortic depressor nerves were cut. Carotid sinuses were connected to a transducer and to a servo-controlled pump system with a short polyethylene tube.

The left greater splanchnic nerve was separated and was cut at the level of diaphragm. A pair of teflon-coated platinum wires was attached to the distal end. The attached ends of platinum wires were embedded in silicone rubber. The free ends of the platinum wires were connected to a constant voltage stimulator, controlled by a computer through a D/A converter.

Carotid sinus pressure was changed at random between 100 to 120 mmHg using a servo-controlled system to determine open-loop baroreflex transfer function ($H_{native}$). Carotid sinus pressure and blood pressure were measured for the determination of the transfer function.

To determine the other transfer function ($H_{STM \to SAP}$), sympathetic nerve activity was changed at random between 0 to 10 Hz while carotid sinus pressure was maintained at 120 mmHg.

The transfer function ($H_{BRP \to STM}$) of vasomotor center, which characterizes the changes in sympathetic nerve activity (STM) in response to pressure on baroreceptors (BRP) was determined as $H_{native}/H_{STM \to SAP}$. Because in native animals the same pressure as blood pressure acts on baroreceptors, the required instantaneous sympathetic nerve activity (STM) to reproduce vasomotor center for given blood pressure changes (SAP) was programmed to calculate according to the following Equation (3).

$$STM(t) = \int_0^\infty h(\tau) \cdot SAP(t-\tau) d\tau \quad (3)$$

(where $h(\tau)$ is impulse response obtained by inverse Fourier transform of $H_{BRP \rightarrow STM}$)

Then, the impaired blood pressure regulation was mimicked by fixing pressure on the baroreceptors isolated from the rest of the circulation; thereby the rats were unable to detect the blood pressure change. Changes in blood pressure of the rats were measured with an artificial pressure sensor-tipped catheter.

To substitute native vasomotor centers, sympathetic nerve activity was predicted by a convolution integral between blood pressure change and the impulse response of the native vasomotor center, and stimulated celiac ganglion, a sympathetic nerve ganglion, according to the predicted value.

How the use of estimated sympathetic nerve activity for the stimulation of celiac ganglion enables the recovery from impaired blood pressure regulation by the improvement of hypotension was evaluated after passive 90-degree head-up tilt tests.

For comparison, normal rats as well as rats with impaired blood pressure regulation also underwent 90-degree head-up tilt tests to evaluate hypotension.

Figure 8:
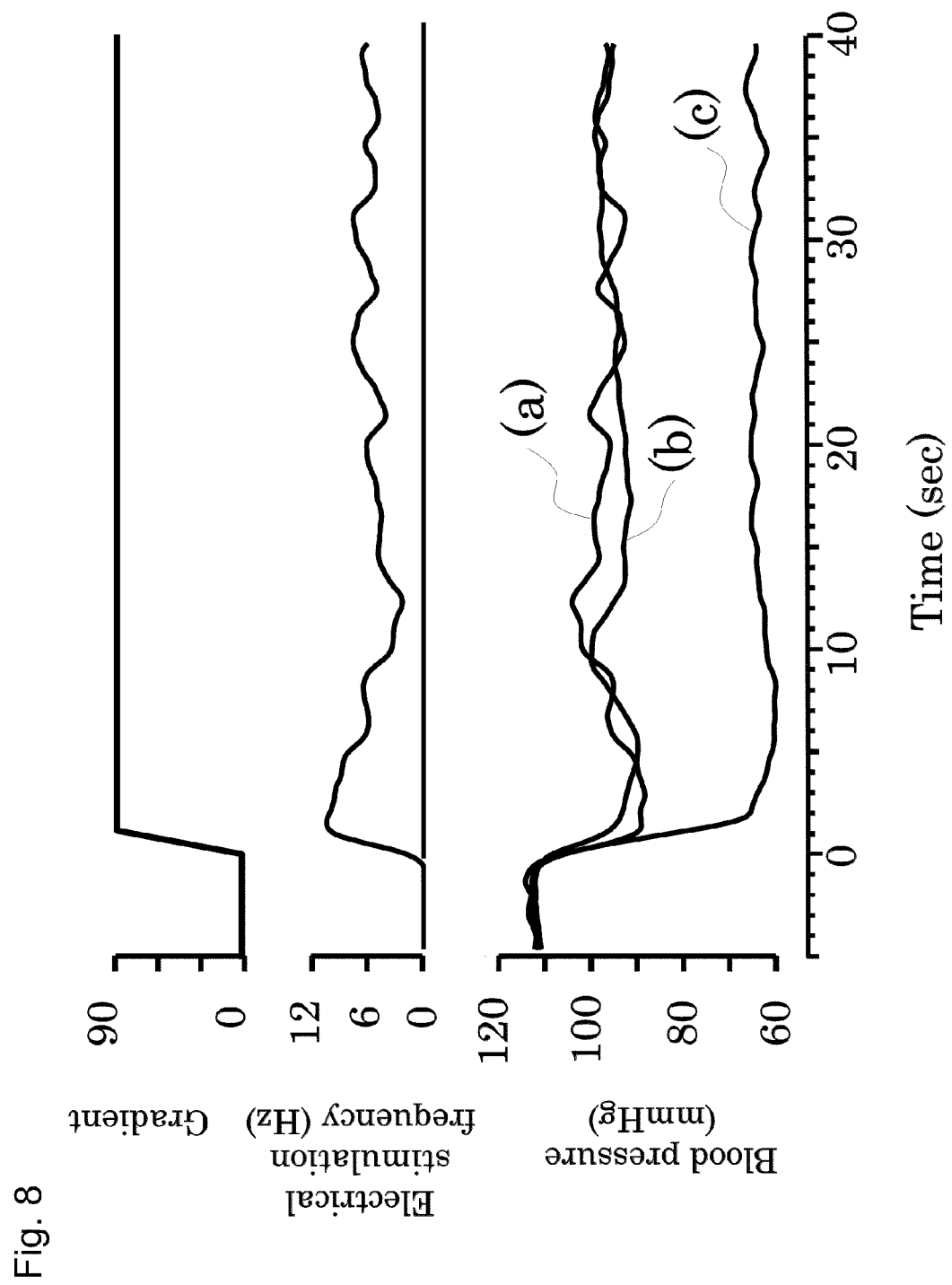
FIG. 8(a) shows orthostatic blood pressure changes of rats with impaired blood pressure regulation but treated with stellate ganglion stimulation in Example 6.
FIG. 8(b) shows orthostatic blood pressure changes of normal rats in Example 6.
FIG. 8(c) shows orthostatic blood pressure changes of rats with impaired blood pressure regulation in Example 6.

The results are shown in FIG. 8. FIG. 8(a) shows the changes in blood pressure of the rats receiving celiac ganglion stimulation, FIG. 8(b) shows the changes in blood pressure of the normal rats, and FIG. 8(c) shows the changes in blood pressure of the rats with impaired blood pressure regulation.

According to the test results in 10 rats, blood pressure decreased by 34±6 mmHg in 2 seconds after head-up tilt, and by 52±5 mmHg in 10 seconds in the rats with impaired blood pressure regulation. On the other hand, blood pressure decreased by 21±5 mmHg in 2 seconds and by 15±6 mmHg in 10 seconds when artificial blood pressure regulation was applied.

As described in detail above, in one embodiment, the heart is paced according to the information from cardiac sympathetic nerve and/or vagal nerve activity, but not based on the nerve activity itself. Instead, it is based on the heart rate estimated from the nerve activity. Therefore, the system is excellent in specificity, sensitivity and transient response.

In another embodiment, sympathetic nerve stimulating signals simulating native regulation are estimated from blood pressure, and the estimated sympathetic nerve stimulating signals, but not blood pressure itself, are used for blood pressure regulation. Therefore, stable blood pressure regulation is possible in the same manner as native regulation.

In another embodiment, the heart is regulated by the native regulatory mechanism when the activity of the heart is normal. The heart is regulated to restore the normal activity when the activity of the heart is abnormal.

The present invention can provide systems to treat diseases by substituting native biological regulatory function. This system can regulate organs as if their central controllers were normally functioning even if the central controllers themselves become abnormal by various causes.

It is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A cardiac pacing system based on biological activities, comprising:
    a) at least one nerve activity sensing means which senses nerve activity of a cardiac sympathetic nerve and/or a vagal nerve, and outputs a plurality of input nerve activity signals;
    b) a calculating means which receives the input nerve activity signals, calculates a transfer function by computing a Fourier transform of normal nerve activity signals and a normal heart rate signal from a normal cardiovascular system, calculates an impulse response by computing an inverse Fourier transform of the transfer function, calculates a plurality of pacing signals for control of a heart rate using a convolution integral between the input nerve activity signals and the impulse response, and outputs the pacing signals; and
    c) a pacing means which receives the pacing signals, and stimulates the heart based on the pacing signals such that heart rate is regulated.

2. The system of claim 1, wherein the pacing means is a cardiac pacemaker.

3. A method of treating cardiac diseases based on biological activities, comprising the steps of:
    a) calculating a transfer function by computing a Fourier transform of normal nerve activity signals and a normal heart rate signal from a normal cardiovascular system and calculating at least one impulse response by computing an inverse Fourier transform of the transfer function;
    b) sensing nerve activity of a cardiac sympathetic nerve and/or a vagal nerve issued by a cardiovascular system, and outputting a plurality of input nerve activity signals;
    c) calculating a plurality of pacing signals for control of a heart rate using a convolution integral between the impulse response and the input nerve activity signals, comprising the substep of discriminating whether the input nerve activity signals are caused by normal cardiovascular activities or by abnormal cardiovascular activities; and
    d) outputting the pacing signals for control of the heart rate only if the input nerve activity signals are determined to be caused by abnormal cardiovascular activities.

4. The method of claim 3, further comprising, after step d), the steps of:
    e) receiving the pacing signals output in step d); and
    f) stimulating the nerve based on the pacing signals output in step d).

* * * * *